United States Patent [19]

Gourlandt

[11] 4,177,810

[45] Dec. 11, 1979

[54] PNEUMATIC INJECTION APPARATUS

[75] Inventor: Albert J. Gourlandt, Gambais, France

[73] Assignee: Damon Corporation, Needham Heights, Mass.

[21] Appl. No.: 881,033

[22] Filed: Feb. 24, 1978

[30] Foreign Application Priority Data

Dec. 23, 1977 [FR] France ............................... 77 39085

[51] Int. Cl.[2] ............................................ A61M 5/00

[52] U.S. Cl. ............................ 128/218 A; 128/218 G

[58] Field of Search .......... 128/218 A, 218 R, 218 G, 128/213, 215, 216, 224, 225, 173 H

[56] References Cited

U.S. PATENT DOCUMENTS

| | | | |
|---|---|---|---|
| 2,918,063 | 12/1959 | Tucker | 128/218 A |
| 3,353,537 | 11/1967 | Knox et al. | 128/218 A |
| 3,424,154 | 1/1969 | Kinsley | 128/173 H |
| 3,526,225 | 9/1970 | Isobe | 128/173 H |
| 3,605,745 | 9/1971 | Hodosh | 128/218 A |
| 3,727,614 | 4/1973 | Kniazuk | 128/218 A |
| 3,964,481 | 6/1976 | Gourlandt et al. | 128/218 A |

*Primary Examiner*—John D. Yasko

*Attorney, Agent, or Firm*—Kenway & Jenney

[57] ABSTRACT

A pneumatic injection apparatus featuring a fluid actuated drive and control system is disclosed. The apparatus, in its various aspects, has a modular construction so that it may be quickly disassembled, both mechanically and pneumatically, for easy maintenance and repair. Thus, for example, a retention means against which an animal part is placed for injection, is pneumatically connected through a release manifold mechanism to permit the retention means to be pneumatically decoupled from the remainder of the apparatus both quickly and easily. The pneumatic drive system is provided with a shock absorbing system to reduce the forces and stresses to which the various syringe elements of the system are subjected. Additionally, a fluid flow path is provided from a presettable counter to the retention means whereby a gas flow is provided when the preset count has been reached.

11 Claims, 7 Drawing Figures

PNEUMATIC INJECTION APPARATUS

The invention relates generally to devices for automatically injecting a treatment liquid by means of a syringe into an animal, and in particular, to a totally pneumatic apparatus for injecting a medicine or vaccine into an animal.

BACKGROUND OF THE INVENTION

In Gourlandt et al, U.S. Pat. No. 3,964,481, issued June 22, 1976, which is incorporated herein by reference, there is described an automatic injection device for injecting a liquid, such as a vaccine or medicine, into an animal retained or held in position on an outer portion of the device. The particularly described apparatus has an electrically operated motor for mechanically driving an injection syringe. The U.S. Pat. No. 3,964,481 states that a fluid-pressure motor could be used. This apparatus provides the means for vaccinating at least about 2000 chicks per hour while at the same time ensuring that an accurate dosage, on the order of one part in one hundred, is injected at an exact location on the animal.

Very often, the automatic injection device of U.S. Pat. No. 3,964,481, referred to above and hereby incorporated by reference, is used at locations remote from electrical power. Under these circumstances, it is desirable to provide a totally fluid driven apparatus, as is provided for in the U.S. Pat. No. 3,964,481; that is, an apparatus which requires no electrical power and which provides the convenience, speed of operation, and precision of the electrically powered device. Such pneumatically controlled apparatus are not only described and claimed in the U.S. Pat. No. 3,964,481, but in addition, at least one United States manufacturer has marketed a pneumatically controlled and operated machine.

A totally pneumatically controlled and actuated machine, however, presents some problems from a practical commercial viewpoint. Without the availability of electrical power, the machine must rely on gas powered devices to perform all of its operating functions. Thus, for example, in order to warn the operator that a predetermined or selected number of chicks have been vaccinated, it is typical to provide a gas operated whistle as the warning signal. Such signals however may cause some confusion and instill fright in the animals being vaccinated. This is, of course, an undesirable side effect.

In addition, a totally pneumatic machine presents some difficulty in cleaning since the mechanical and pneumatically connected portions are often difficult or cumbersome to disconnect and disassemble. Furthermore, it is particularly important to have the retention means described in the U.S. Pat. No. 3,964,481 available and easily removable for cleaning, because this portion of the apparatus is likely to require more frequent routine maintenance than the other portions of the apparatus which are fully enclosed within the apparatus housing.

It is necessary also, in the earlier described pneumatic systems, to provide careful inspection of the pneumatic drive system since the forces and stresses arising in the pneumatic system are often greater than the forces and stresses arising in the corresponding electrically driven systems.

Principal objects of this invention are therefore to provide a pneumatically operated injection apparatus having a modular construction, and in particular, wherein the retention means may be quickly and easily disconnected, both mechanically and pneumatically, from the rest of the apparatus; wherein a silent signaling means is provided to signal the termination of a series of injections; and wherein means are provided to reduce the wear and stresses on the driven mechanical components of the pneumatic system. Further objects of the invention include providing a pneumatically operated injection apparatus which is reliable, which has a minimum number of moving parts, which can be easily disassembled, which has a minimum cost, which provides accurate and precise positioning of the animal part to be injected, which provides an accurate dosage during injections, which is portable, and which can be reliably operated by unskilled personnel.

SUMMARY OF THE INVENTION

An automatic injection apparatus according to the present invention features a fluid actuated drive cylinder having a driven rod extending from one end thereof, the rod translating along a longitudinal axis of the cylinder upon actuation of the cylinder. A syringe displacement means is connected to the rod for movement along the longitudinal axis of the displacement means, and an injection syringe is connected to and driven by the syringe displacement means. The injection syringe has a syringe body slidably mounted within a syringe support, a syringe piston slidably mounted within the syringe body, and an injection needle rigidly secured to the syringe body. The syringe body is also provided with a lateral injection-liquid supply tubulure. The apparatus further features a fluid logic circuitry which has a pneumatic switching means for switchably connecting a system fluid input to the drive cylinder for repetitively driving and releasing the cylinder. The switching means includes at least a start switching means and preferably also a stop switching means. The cylinder is thus urged from a withdrawal state, in which the needle is withdrawn, to an injection state in which the needle is displaced forward, and back to the withdrawal state, etc. The cylinder is driven into the injection state in response to actuation of the start switching means. If a stop switching means is provided, the cylinder is urged into the release state in response to activation of the stop switching means (even if the start switching means is still actuated). If a stop switching means is not provided the translational displacement of the syringe may be fixed by the mechanical constraints of the drive system.

The start switching means, which is normally in a ready state, corresponding generally to the withdrawal state of the cylinder, is actuated to a start state, corresponding generally to the injection state of the cylinder, when an animal part is placed in position at the retention means. The retention means houses the start switching means and provides at least one surface against which a part of the animal to be treated is immobilized. The retention means is releasably secured to a top panel surface of the apparatus.

The apparatus further features a release manifold mechanism for connecting the start switching means to other portions of the fluid logic circuitry, whereby the retention means can be easily disconnected, both mechanically and pneumatically, from the rest of the apparatus.

In another aspect of the invention, there is featured as part of the fluid logic circuitry, means associated with the pneumatic switching means for incrementing a presettable counter. The presettable counter provides, when a preset selected count is reached, a through fluid flow path from a counter input to a counter output. A fluid flow line connects the counter output to the retention means through the release mechanism, and the retention means includes a fluid path for channeling a jet of gas from the connecting flow line to the surface against which the animal part is retained. Thereby, a jet of gas may be directed against a retained animal part or may provide a silent warning against initiating further injections after the preset count is reached. Preferably, the presettable counter is incremented by a gas flow associated with the pneumatic switching means.

In another aspect of the invention, the fluid actuated drive cylinder, the syringe displacement means, the injection syringe, and the retention means are each self-contained modular units which can be quickly disconnected, both pneumatically and mechanically, from each other.

In yet another aspect of the invention, there is featured a shock-absorbing means positioned between the drive cylinder and the injection syringe for reducing the forces and stresses to which the injection syringe is subjected.

DESCRIPTION OF THE DRAWINGS

Other objects, features, and advantages of the invention will appear from the following description of a preferred embodiment of the invention taken together with the drawings in which.

DESCRIPTION OF A PREFERRED EMBODIMENT

General Structure

Figure 1:
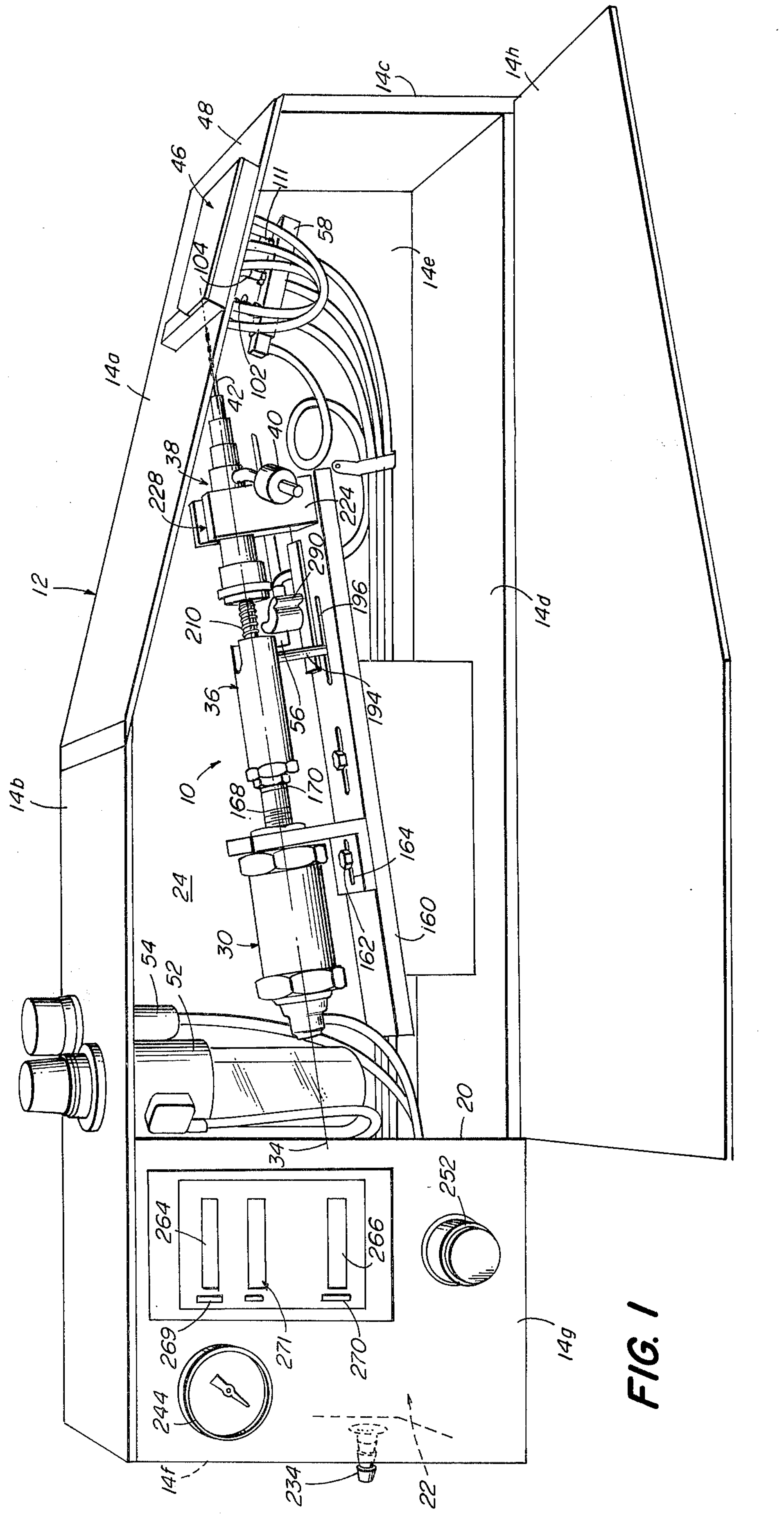
FIG. 1 is a side perspective view of a preferred construction of the injection apparatus showing in particular the pneumatically driven mechanical drive system of the apparatus.

The automatic injection apparatus 10 is housed in a casing 12 having a plurality of side, top and bottom panels 14*a*, 14*b*, . . . , 14*h*, and a partitioning panel 20. Partitioning panel 20 divides the interior of the casing 12 into two sections, a fluid logic section 22 and a pneumatic drive section 24.

Figure 6:
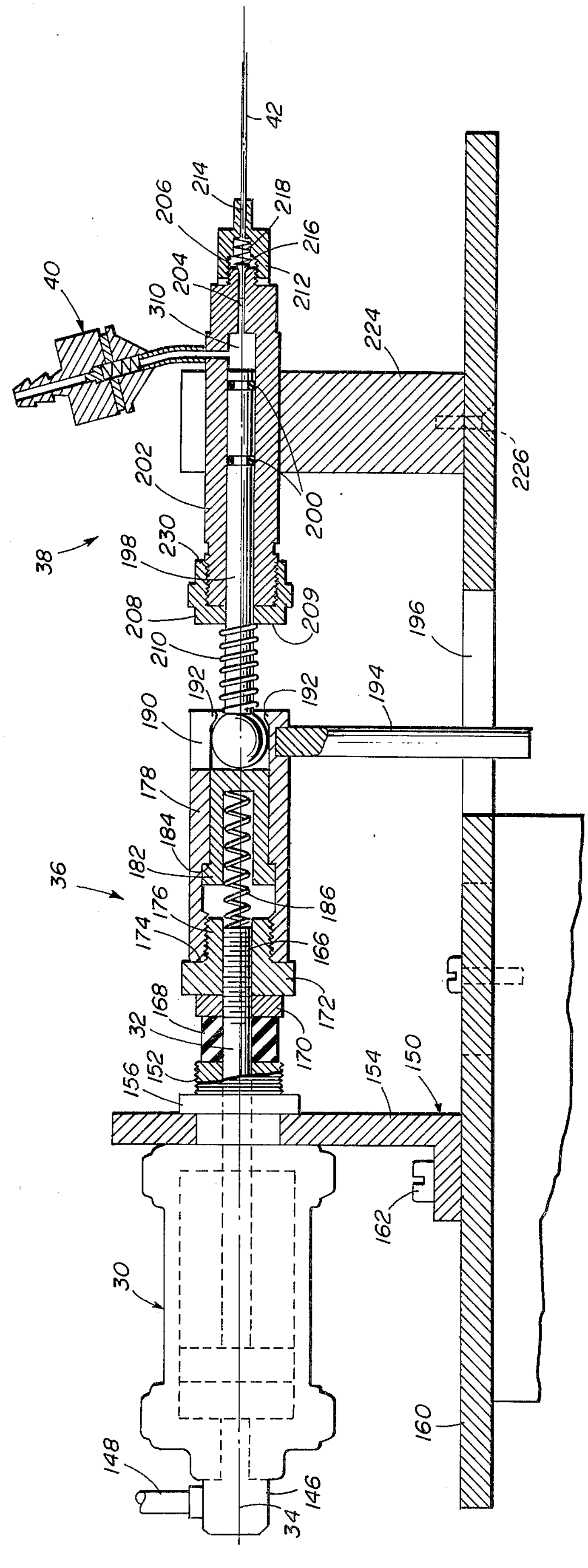
FIG. 6 is a cross-sectional view of the mechanical drive system according to a preferred embodiment of the invention.

The fluid logic section 22 houses most of the fluid logic circuitry required to instrument and control operation of the apparatus. The pneumatic drive section 24 houses primarily the mechanical drive system. A fluid actuated drive cylinder 30 having a driven rod 32 translates along a longitudinal axis 34 of the cylinder upon actuation of the cylinder (FIG. 6). The pneumatic drive section further contains a syringe displacement means 36 connected to the rod 32 for movement, in this embodiment, along the longitudinal axis 34 of the cylinder, and an injection syringe 38 connected to and driven by the syringe displacement means 36. A lateral injection-liquid supply tubulure 40 is connected to the injection syringe for supplying the liquid which will be injected into the animal. The injection syringe has secured at its forwardmost end a needle 42 which is translated through an aperture 44 (FIG. 2) in the top panel 14*a* to inject the liquid into an animal part being held against a retention means 46 secured against an outside wall portion 48 of the casing. The elements of the pneumatic section 24 are constructed in a modular form so that they can be easily disconnected both pneumatically and mechanically, for ease of maintenance and repair. The pneumatic section 24 also houses a fluid regulator-filter 52, a fluid signaling device 54, a cam operated fluid stop switch 56, and a release manifold mechanism 58, all of which form a part of the fluid logic circuitry.

The Retention Means

Figure 2:
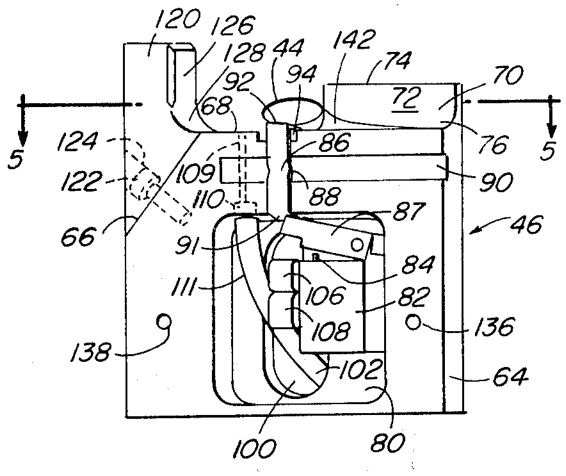
FIG. 2 is a top plan view of the retention means according to the invention with the top cover removed.

Referring to FIG. 2, the retention means 46 comprises a thick plate 64, made, for example, of a lightweight alloy, having a substantially square or rectangular shape and having a planar main abutment face 66 and a planar first auxiliary abutment face 68, the two faces 66 and 68 forming an obtuse angle. Plate 64 further has an auxiliary portion 70 integral therewith. An elongated external surface 72 of the portion 70 is planar towards its external edge 74 and joins the abutment face 68 along a fraction of the length of the latter by an arcuate surface portion 76.

The thick plate 64 has an internal cavity 80 which contains a pneumatic start switch 82. Switch 82 has a movable element 84 which can be actuated by a push button 86 acting upon a pivoted cam member 87. Push button 86 is U-shaped, a central branch 88 of the U-shaped push button being located in a groove 90 of the plate 64. One of the lateral branches 91 of the "U" is in contact with the pivoted cam member 87 and the other branch 92 of the "U" is more or less "introduced" into a cavity 94 over the whole height of the abutment face 68 and is pushed or urged towards the bottom of cavity 94. When the movable element 84 is pushed (downward in FIG. 2), thereby actuating pneumatic start switch 82, the injection operation is immediately started. The pneumatic start switch is generally actuated through movable element 84 when a limb or other part of an animal is applied against the abutment face 68.

Cavity 80 has an aperture 100 through which at least two flexible tubular conduits 102, 104 pass and connect to the pneumatic start switch 82 inside the cavity 80 at terminals 106, 108 respectively. It is through these tubular conduits that the pneumatic start switch is connected to the rest of the fluid circuitry to control the beginning of each injection operation as described in more detail below..

Plate 64 further has a narrow fluid flow path 109, extending through the interior of plate 64. Path 109 has a larger diameter opening 110 facing aperture 80. A flexible tubing 111, extending through aperture 100 from release manifold mechanism 58 makes a press fit at opening 110. Thereby, when a preselected number of injections have been made, a flow of gas is provided from the exit opening of path 109 at abutment face 68 as described in detail below.

Figure 3:
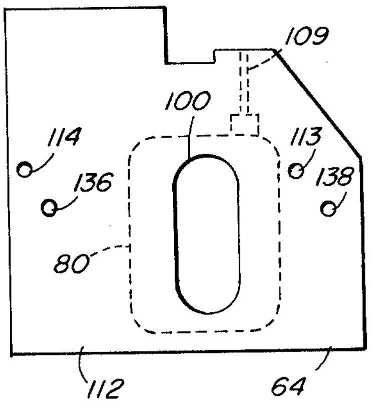
FIG. 3 is a bottom plan view of the retention means with the pneumatic related components removed for clarity.

FIG. 3 shows the lower or bottom surface 112 of plate 64 which is normally applied against the top pivotal panel 14a. The surface 112 is secured on panel 14a, by, for example, threaded rods 113, 114 which may be engaged by serrated or embossed nuts 116, 118.

Figure 4:
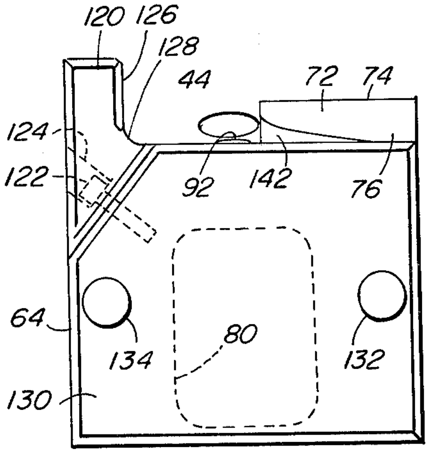
FIG. 4 is a top plan view of the retention means with the top cover in place.

Referring to FIGS. 2 and 4, the retention means is also provided with a removable member 120 which is rigidly secured to thick plate 64 along the abutment face 66 by means of a screw 122, the head of which is located in a duct 124 of member 120. The screw head rests on an inner peripheral shoulder of the duct. The thickness of member 120 is substantially the same as that of the thick plate 64 so that continuity is ensured from the abutment face 68 of plate 64 to a short abutment plane face 126 of the member 120 by an interconnecting arcuate face 128.

The thick plate 64 is also provided with a top cover 130 having a bevelled peripheral edge. Cover 130 is secured to plate 64 by screws 132, 134 having serrated or knurled heads. Screws 132, 134 are screwed into threaded bores 136, 138 respectively of plate 64 (FIGS. 2 and 3).

Figure 5:
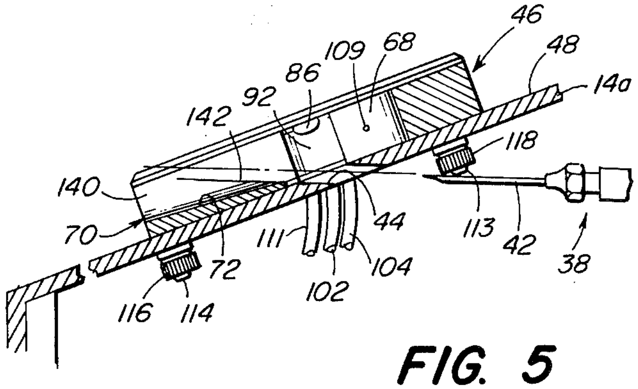
FIG. 5 is a cross-sectional view along lines 5—5 of FIG. 2.

Referring to FIG. 5, the interrelationship of the components of retention means 46 of FIGS. 2–4 with respect to the top panel 14a, including the aperture 44 and the needle end of the injection syringe, in the injection state, is shown. The injection syringe 38 with its needle 42 is adapted to pass through aperture 44 as noted above. An incurved surface portion 140 of auxiliary portion 70 is slightly bevelled in its lower portion, the bevelling plane being referred to by a number 142. Incurved surface portion 140 is also slightly inclined to the exterior surface of the top panel 14a.

The Mechanical Drive System

Referring now to FIG. 6, the fluid actuated drive cylinder 30 is provided with a fluid pressure input, preferably compressed air, through an inlet valve 146 from a flexible supply conduit 148. Cylinder 30 is a standard, commercially available cylinder, such as those manufactured by Schrader Manufacturing Company having manufacturing offices located worldwide. The cylinder 30 is secured to and supported by a cylinder support member 150. A threaded support end 152 of cylinder 30 extends through an aperture in a vertically disposed portion 154 of support 150 and is secured thereto by a nut 156 threaded onto the threaded support end 152 of cylinder 30. The cylinder support 154 is bolted to a main body support plate 160 by screws 162 extending through slotted apertures 164 in member 150.

Extending outward past the threaded support end 152 of cylinder 30 is the driven rod 32 of the cylinder. Driven rod 32 is threaded at its driving end 166.

The syringe displacement means 36 comprises a first shock absorbing member 168 which, in the illustrated embodiment, makes a press fit with an unthreaded portion of rod 32, has a substantially hollow cylindrical shape, is mounted adjacent threaded support end 152, and is held in place by a nut 170. Member 168 may be composed of any suitably resilient material, for example, a hard rubber compound. A threaded size converting member 172 is threaded onto end 166 of rod 32 and is tightened and secured against nut 170. Member 172 has an annular abutment shoulder 174 and a threaded portion 176 which is engaged by a hollow displacement member 178.

Positioned within hollow member 178 is a second hollow member 180 having an enlarged portion 182 which rests against an abutment shoulder 184 of hollow member 178. Hollow member 180 is forced forward in hollow member 178 by a stiff shock absorbing spring 186 which engages rod 32 at one end and the forward interior surface of hollow member 180 at its other end.

The forward end of hollow member 178 has a substantially circular shaped top opening 190 which allows a ball shaped end of injection syringe 38 to be pivotably and releasably press fit into the hollow forward portion of member 178. The ball shaped portion is held within the hollow forward portion by inwardly directed lips 192 of member 178. Hollow member 178 further has a downwardly extending rod member 194 which passes through an aligned slotted aperture 196 in the main body support plate 160.

The injection syringe 38 comprises a rod or piston member 198 which has, at its forward end, two spaced apart "O" rings 200 which sealingly mate with the interior surface of a hollow syringe body member 202. Body member 202 has a narrow cylindrical passage 204 at its forward end which terminates in a narrow, exteriorly threaded, forward portion 206. The rearward portion of body member 202 is also threaded and seats in the internal threads of a C-shaped cup member 208. Cup member 208 has an aperture in its body portion 209 through which rod member 198 passes. A spring 210 is provided between C-shaped cup member 208 and the ball shaped end of rod 198. Threaded onto the forward end of body member 202 is a hollow syringe member 212 having a constricted opening 214 at its forward end. Seated within the narrowed cylindrical passage 204 of hollow member 202 is a plunger shaped element 216, held in position by a spring member 218. The needle 42 is secured in constricted opening 214.

The injection syringe member 38 is slidably supported by a grooved syringe support member 224 secured to main body support plate 160, for example by screws 226. The body member 202 makes a sliding fit within a grooved portion 228 of support member 224 which allows the injection syringe to slidably translate in response to a driving force provided through rod 198 and spring 210. The amount of displacement of the injection syringe body member 202 is limited because a forward end 230 of C-shaped cup member 208 engages the support member 224 during its forward movement.

The injection syringe can also be pivoted upward, away from the support 224 and about the ball shaped or spherical end of rod 198 to enable the syringe members to be more easily accessed and maintained.

The Fluid Circuit

Figure 7:
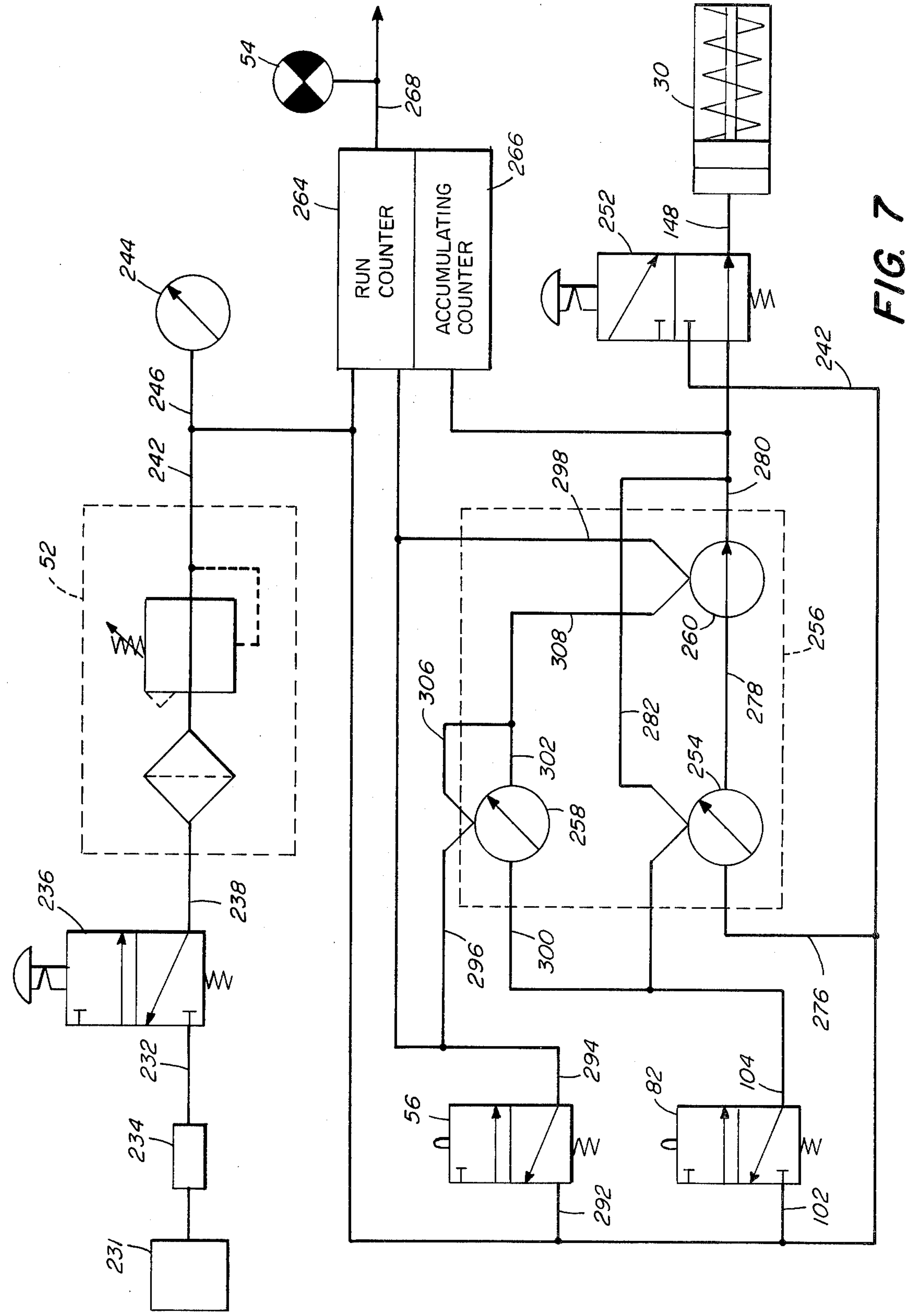
FIG. 7 is a circuit diagram of the pneumatic flow paths according to a preferred embodiment of the invention.

Referring now to FIG. 7, the pneumatic components are configured in a circuit for effecting repetitive actuation of the drive cylinder 30. An external high pressure fluid source 231, preferably compressed air, is connected to an internal input conduit 232 through an input terminal 234 attached to the casing 12 at side panel 14f. A push-button pneumatic switch or circuit breaker 236 is connected to the input terminal 234 through conduit 232 and provides an on-off control for the entire system. The output of the push-button switch, through a conduit 238, is filtered and regulated to a reduced pressure by the filter-regulator 52 which is a commercially available unit such as, for example, Schrader Scovill Type No. B 260C. The output of the filter-regulator is provided over conduit 242 and is regulated to an operating pressure of about 50 p.s.i., for the illustrated embodiment. The output of filter-regulator 52 is monitored by a pressure gauge 244 which is connected to conduit 242 through a flexible conduit 246. (The pressure gauge is mounted on front panel 14g.) The output of the filter-regulator is also connected to the pneumatic start switch 82, the pneumatic stop switch 56, a second pneumatic push-button circuit breaker or switch 252, and to the input of a fluid logic element 254 of a fluid logic element configuration 256.

Before describing the fluid circuit further, the function of the three logic elements, elements 254, 258, and 260 of the fluid logic element configuration 256 will be explained. Each logic element can be visualized as a normally open or a normally closed fluid valve, that is a normally open switch in which fluid passes or a normally closed switch in which fluid does not pass. In the schematic representation of the fluid elements, the input to each fluid element is represented by the line appearing at the "nine o'clock" position of the circle representing the element. The output line for each of the elements is the line appearing at the "three o'clock" position of the circle, and the control lines for each element appear at the "twelve o'clock" position for each of the circle representations. There are two control lines for each logic element, the two control lines being connected substantially parallel.

Logic elements 254 and 258 are identical in function. Each of these logic elements is normally closed or in a non-passing state. When a fluid pressure is applied to either of the control line inputs of the logic elements 254, 258, the element changes its state to a normally open state in which fluid is passed. Logic element 260 is a normally open logic element, that is, one in which fluid is normally passed; and if a pressure is applied to either of its control line inputs, the logic element changes to a closed or non-passing state.

The fluid circuit, in the preferred embodiment, further includes two counters, a run counter 264 and cumulative counter 266, which register respectively the number of doses administered during a run and the total number of doses administered over a selected time span, for example one day. Run counter 264 is especially useful because in the preferred embodiment it is preset to a selected number whereby, when the counter reaches that number, a gas flow through an output conduit 268 is initiated. It is the gas flow through conduit 268 which provides, through conduit 111, the gas flow at flow path 109 of the retention means. Additionally, the fluid flow over line 268 may also be connected to a visual fluid signaling device or indicator 54 to signal that the preselected number of injections has been reached.

System Operation

In operation, the apparatus is made operational by "turning on" switch 236 to provide fluid pressure in conduit 238. The counters may be manually reset by depressing front panel buttons 269,270. The run counter may be reset at the end of every run and the cumulative counter at the beginning of the selected longer time span. The number of injections to be allowed for each run is set in selector 271, a part of counter assembly (FIG. 1), and the retention means is aligned with the injection needle. The machine is then ready to be used.

The first animal is positioned at the retention means, and in doing so, the push-button operated pneumatic start switch 82 is opened, i.e. passes fluid, thereby providing fluid pressure at its output on conduit 104. The pressure in conduit 104 causes logic element 254, which had been in its normally closed state, to open, and allows high pressure gas to pass from its input conduit 276 to its output on a conduit 278. Since fluid element 260 is in a normally open state, high pressure fluid passes through element 260 to an output conduit 280. The pressure in conduit 280 (1) actuates the accumulating counter for one count, (2) is fed back to logic element 254 over a conduit 282 to maintain element 254 in an open state even if the start switch 82 is thereafter released and (3) is also provided as an input to switch 252 which, in its normal operating condition, provides a through path to its output, and via conduit 148, to cylinder 30.

In response to the fluid input over conduit 148, the cylinder 30 is actuated causing its rod member 32 to be displaced from its normal withdrawal state in the forward direction to an injection state. As rod member 32 is initially displaced in the forward direction, so are syringe displacement means 36 and injection syringe 38, and as the displacement means 36 and hence injection syringe 38 are urged forward, the forward end 230 of C-shaped member 208 engages syringe support member 224, which stops the forward motion of body member 202. (This determines the forwardmost needle position.) The syringe displacement means is, however, still urged forward (driving rod 198 forward with respect to body member 202) until the downwardly extending vertical rod member 194 sufficiently engages a camming element 290 of the pneumatic stop switch 56 to open switch 56 and thus signal the end of forward travel of rod 32.

When switch 56 is opened by the action of rod 194 against camming element 290, fluid pressure, provided at the switch input over a conduit 292, is reflected at its output in a flexible conduit 294. In response to the fluid pressure in conduit 294, run counter 264 is incremented by one count, and fluid pressure is applied to the control input of logic elements 258 and 260 over conduits 296 and 298 respectively. In response, elements 258 and 260 change their state: element 258 changes from a normally closed state to an open state thereby allowing fluids to pass from its input over a conduit 300 from the start switch to its output over a conduit 302; and normally open (fluid passing) logic element 260 changes to a closed state thereby stopping fluid flow through the switch.

When logic element 260 changes to a closed state, the supply of fluid pressure to the cylinder 30, through switch 252, is terminated and rod 32 therefore stops its forward motion and will begin to retract. When element 258 changes to an open state in response to actuation of the stop switch, pressure from the output of start switch 82 over line 104 is transmitted through the logic element 258 and provides pressure at a control input of the logic element 258 over a conduit 306 and at a control input of logic element 260 over a conduit 308. Thereby, even after the pressure provided by opening switch 56 terminates (as the cylinder 30 causes its rod 32 to retract), elements 258 and 260 will continue to have a pressurized control input so long as start switch 82 is actuated by the presence of an animal part against push button 86 at the retention means. In this manner, there will be provided only one injection for each animal no matter how long the animal is maintained in position against switch actuating push button 86.

As noted above, when run counter 264 reaches the preselected count, it initiates a visual and an air flow signaling system to warn the operator that the preselected number has been reached.

As described in detail in the referenced Gourlandt et al, U.S. Pat. No. 3,964,481, operation of cylinder 30 by displacement of its rod 32 initiates a "dual displacement" of the displacement means 36 and injection syringe 38. Thus, as rod 32 moves forward, the displacement means 36 and the injection syringe 38 are displaced in a forward direction, substantially as a unit, until C-shaped cup member 208 engages syringe support member 224 whereby movement of hollow body member 202 terminates. However, the rod 32 continues to move forward, forcing displacement means 36 to move forward. As a result, second hollow member 180 acts on the ball shaped end of rod shaped member 198 with a predetermined pressure fixed by spring 186 (which also absorbs some of the "shock" when C-shaped cup 208 engages the syringe support), to force rod 198 forward relative to body member 202. Thereby, a measured quantity of vaccine or other liquid, supplied by tubulure 40 to fill hollow chamber 310, is forced out through the injection needle 42, which by that time, has already pierced the skin of the animal positioned at the retention means.

The apparatus can also be manually tested using the switch or circuit breaker 252. By depressing the actuating push button of switch 252, the output conduit 148 is connected to pressurized conduit 242. As a result, the injection syringe is displaced to its injection state by rod 32 and rod 32 is urged to its forward-most position. In this manner the mechanical drive system and the retention means can be aligned with each other and with aperture 44.

Other embodiments of the invention will be obvious to those skilled in the art and any additions, subtractions, deletions, or other modifications of the disclosed preferred embodiment of the invention are within the scope of the following claims.

What is claimed is:

1. An automatic injection apparatus comprising
  - a fluid actuated drive cylinder having a driven rod extending from one end thereof, said rod translating along a longitudinal axis of said cylinder upon actuation of said cylinder,
  - a syringe displacement means connected to said rod for movement along the longitudinal axis of the displacement means,
  - an injection syringe connected to said displacement means and having
    - a syringe body slidably mounted within a syringe support, and being provided with a lateral injection-liquid supply tubulure,
    - a syringe piston slidably mounted within the syringe body, and
    - an injection needle rigidly secured to the syringe body,
  - fluid logic circuitry including a pneumatic switching means for switchably connecting a system fluid input to said drive cylinder for repetitively driving and releasing said cylinder,
  - said switching means including at least a start switching means and said cylinder being urged from a withdrawal state to an injection state in response to actuation of said start switching means,
  - retention means for immobilizing a part of an animal to be treated, said start switching means being housed in said retention means, and said retention means being releasably secured to a top panel surface of said apparatus,
  - said start switching means being normally in a ready state and being actuated to a start state when said animal part is placed in position at said retention means, and
  - a release manifold mechanism for connecting said start switching means to other portions of said fluid logic circuitry,
  - whereby said retention means can be quickly disconnected both mechanically and pneumatically from the rest of said apparatus.

2. The automatic injection apparatus of claim 1 wherein said fluid logic circuitry further comprises
  - means associated with the pneumatic switching means for incrementing a presettable counter,
  - said presettable counter providing a through fluid flow path from a counter input to a counter output when a preset selected count is reached,
  - a fluid flow line connecting said counter output to said retention means through said release manifold mechanism, and
  - said retention means having a fluid path for channeling a jet of gas from said connecting flow line to the surface against which said animal part is retained,
  - whereby a jet of gas may be directed to provide a warning against initiating further injections after said preset count is reached.

3. The automatic injection apparatus of claim 2 further including
  - a visual signaling device connected to said counter fluid flow line and responsive to fluid pressure in said line for providing a visual indication of the presence of at least a minimum known pressure.

4. The automatic injection apparatus of claim 2 wherein said retention means fluid path is contained internally of said retention means.

5. The automatic injection apparatus of claim 2 wherein said retention means fluid jet is positioned to direct said gas against said animal part when said part is positioned adjacent said starting switch.

6. The automatic injection apparatus of claim 1 wherein said fluid actuated drive cylinder, said syringe displacement means, said injection syringe, and said retention means each comprise self-contained modular units which can be quickly disconnected, both pneumatically and mechanically, from each other.

7. The automatic injection apparatus of claim 6 further comprising
  - a pivoting releasable connection between the injection syringe and the syringe displacement means,
  - whereby the injection syringe can be pivoted to a position in which it can be more easily accessed.

8. An automatic injection apparatus comprising
  - a fluid actuated drive cylinder having a driven rod extending from one end thereof, said rod translating along a longitudinal axis of said cylinder upon actuation of said cylinder,
  - a syringe displacement means connected to said rod for movement along the longitudinal axis of the displacement means,
  - an injection syringe connected to said displacement means and having
    - a syringe body slidably mounted within a syringe support, and being provided with a lateral injection-liquid supply tubulure,
    - a syringe piston slidably mounted within the syringe body, and
    - an injection needle rigidly secured to the syringe body, fluid logic circuitry including a pneumatic switching means for switchably connecting a fluid input valve to said drive cylinder for repetitively driving said cylinder, said switching means including at least a start switching means and said cylinder being urged from a withdrawal state to an injection state in response to actuation of said start switching means, retention means for immobilizing a part of an animal to be treated, said start switching means being housed in said retention means, and said retention means being releasably secured to a top surface portion of said apparatus, said start switching means being normally in a ready state and being actuated to a start state when said animal part is placed in position at said retention means, and shock absorbing means positioned between the drive cylinder and the injection syringe for reducing the acceleration forces to which said injection syringe is subjected.

9. The apparatus of claim 8 wherein said shock absorbing means is a resilient hollow cylindrical member mounted coaxially on the cylinder rod.

10. The apparatus of claim 9 wherein said shock absorbing means is a resilient spring member retained between the cylinder rod and the displacement means.

11. An automatic injection apparatus comprising a fluid actuated drive cylinder having a driven rod extending from one end thereof, the rod translating along a longitudinal axis of the cylinder upon actuation of the cylinder, a syringe displacement means driven by the rod for movement along a longitudinal axis of the displacement means, an injection syringe releasably and pivotably connected to the displacement means and having a syringe body slidably mounted within a syringe support and being provided with a lateral injection-liquid supply tubulure, a syringe piston slidably mounted within the syringe body, and an injection needle rigidly secured to the syringe body, fluid logic circuitry including a pneumatic switching means for switchably connecting a system fluid input to the drive cylinder for repeatedly driving the cylinder to a forward injection state, the switching means including at least a start switching means and a stop switching means and the cylinder being urged from a withdrawal state to an injection state in response to actuation of the start switching means and from the injection state to the withdrawal state in response to actuation of the stop switching means, retention means, releasably connected to a top panel surface of said apparatus, and having a surface against which to immobilize a part of an animal to be treated, and the start switching means being housed in the retention means, the start switching means being normally in a ready state and being actuated to a start state when the animal part is placed in position at the retention means surface, a release manifold mechanism for connecting the start switching means to the remainder of the fluid logic circuitry, means associated with the pneumatic switching means for incrementing a presettable counter, the presettable counter providing a through fluid flow from a counter input to a counter output when a preset selected count is reached, a fluid flow line connecting the counter output to the retention means through the release manifold mechanism, the retention means further having an internal fluid path for channeling a gas flow from the connecting flow line to the surface against which animal part is retained for injection, whereby the retention means can be easily disconnected, both mechanically and pneumatically, from the rest of the apparatus and a jet of gas may be directed to provide a warning against initiating further injections after the preset count has been reached.

* * * * *